(12) United States Patent
Reeves

(10) Patent No.: US 6,747,561 B1
(45) Date of Patent: Jun. 8, 2004

(54) BODILY WORN DEVICE FOR DIGITAL STORAGE AND RETRIEVAL OF MEDICAL RECORDS AND PERSONAL IDENTIFICATION

(75) Inventor: William Francis Reeves, N. Branford, CT (US)

(73) Assignee: Med-Datanet, LLC, North Branford, CT (US)

( * ) Notice: Subject to any disclaimer, the term of this patent is extended or adjusted under 35 U.S.C. 154(b) by 378 days.

(21) Appl. No.: 09/597,107

(22) Filed: Jun. 20, 2000

(51) Int. Cl.[7] .............................................. G08B 23/00
(52) U.S. Cl. ................... 340/573.1; 340/573.5
(58) Field of Search .......................... 340/573.1, 573.7, 340/691.1, 573.5, 573.6, 573.4; 128/903; 600/300, 459, 437

(56) References Cited

U.S. PATENT DOCUMENTS

| | | | |
|---|---|---|---|
| 5,830,548 A | * 11/1998 | Andersen et al. | 428/36.4 |
| 5,986,562 A | * 11/1999 | Nikolich | 340/572.7 |
| 6,175,124 B1 | * 1/2001 | Cole et al. | 257/48 |
| 6,294,999 B1 | * 9/2001 | Yarin et al. | 340/573.1 |
| 6,375,612 B1 | * 4/2002 | Guichon et al. | 600/300 |
| 6,380,858 B1 | * 4/2002 | Yarin et al. | 340/573.1 |

* cited by examiner

Primary Examiner—Van Trieu

(57) ABSTRACT

The invention is a novel bodily worn device, preferably in the form of jewelry, a medallion or watch, which provides for the digital storage and retrieval of a user's medical records, drug prescriptions, medical history, organ donor instructions, and personal identification for use in an emergency or routine medical situation. Additional embodiments include an electronic dog-tag for military and law enforcement applications. The device includes: an outer safety shell, in the form of a medallion, or watch with markings which identify it as a medical device, and a digital storage media such as a computer chip or high density silicon media, and non-contact wireless electrical power to the device and non-contact wireless retrieval of records. Security features include encrypted software and user password for medical records confidentially. The invention includes features for retrieving and displaying stored records on computer screens via a wireless interface wand or by providing access to a central website via the Internet with use of a user serial number password.

61 Claims, 9 Drawing Sheets

| PHOTO I.D. | FINGER PRINT | IRIS PRINT | DENTAL RECORDS | SAMPLE ECG ULTRASOUND |
|---|---|---|---|---|
| EMERGENCY MECIDAL RECORDS BLOOD TYPE DRUG REACTIONS PRE-EXISTING CONDITIONS ||||||
| EMERGENCY TREATMENT INSTRUCTIONS: PHYSICIAN PRE-EXISTING CONDITIONS ||||||
| ORGAN DONOR INSTRUCTIONS: ||||||
| LIVING WILL INSTRUCTIONS: ||||||

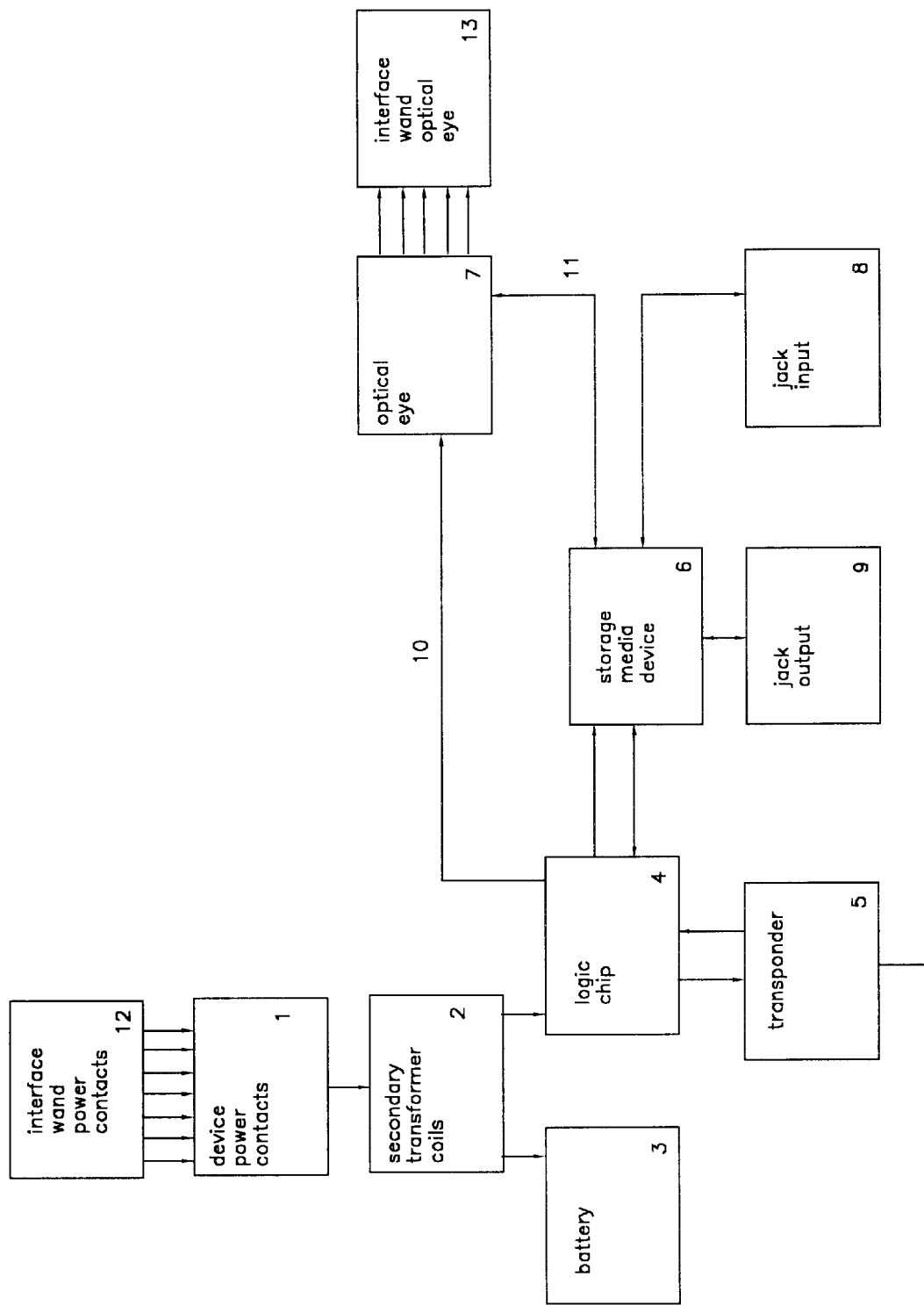
PAT. FG. 9

BODILY WORN DEVICE FOR DIGITAL STORAGE AND RETRIEVAL OF MEDICAL RECORDS AND PERSONAL IDENTIFICATION

CROSS REFERENCE TO RELATED APPLICATIONS

This patent application is related to U.S. patent application Ser. Nos. 09/578,664 and 09/583,336 and U.S. Pat. No. 6,467,690.

STATEMENT REGARDING FEDERAL RESEARCH

Not Applicable

MATERIAL SUBMITTED ON COMPACT DISK

Not Applicable

BACKGROUND OF THE INVENTION

The present invention relates to novel and improved methods of bodily worn or hand held devices which useful for the digital storage and retrieval of medical records, prescription history and emergency medical instructions in the event the wearer of such a device experiences a medical emergency, accident, or any other emergency. The device can provide a positive identification of the wearer via digitally stored color photo, in the event the wearer is unconscious and requires emergency medical treatment and/or medication provider wants to make a positive identification. The device can also be linked to the Internet via a serial number code to augment the digital storage capacity and international accessibility of said medical records and personal information in an emergency situation.

There is a long history of devices and particularly jewelry which are bodily worn and have been used to identify persons with known medical conditions in the event of a medical emergency. Several such examples of this would be a bracelet for identifying a rare blood type or a bracelet for identifying a diabetic or person with a rare allergic reaction to bees, snake bites or spiders.

Some recent patents which relate to bodily worn devices for medical records make reference to storing the medical records on microfilm (Chioffe U.S. Pat. No. 4,249,330 and Pelosi U.S. Pat. No. 5,359,798) or on a fan like device which could be read by a medical person (Eller U.S. Pat. No. 4,984,683). These inventions would be awkward to use and read in the event of an emergency and would only provide very limited medical information in the event of an emergency. Also, in the event of an accident, wherein these devises came off a persons body and the person was unconscious, it would be impossible for a medical emergency person to know which victim the jewelry belonged to (no positive ID).

Other recent patents include medical cards or medical like credit cards (Eberhardt U.S. Pat. No. 5,659,741 and Whalen U.S. Pat. No. 5,197,763) wherein medical records can be imbedded on or written into the card for storage and carrying in a wallet. The shortcoming of such cards, in the event of a medical emergency, is that such cards which are carried in a wallet would not be accessible to or known by the medical emergency worker. Having to require a medical worker or emergency technician to reach into an unconscious persons wallet to search for medical card poses serious legal liability questions, not to mention the awkwardness of fumbling with a persons wallet and searching through credit cards in an emergency. This card approach to the problem is not a practical solution which would be adopted by US society in general and particularly the medical-legal communities because of the legal questions. What if a medical technician was to find illegal drugs or weapons on a person when searching in their pockets or purse for a medical card? Although Eberhardt does mention in one sentence a locket or bracelet device he fails to teach or describe the invention disclosed herein or address the issues of being rugged, waterproof, explosion proof or bullet proof or address any of the issues of a transponder for tracking or locating ill, dead or lost wearers of the device.

Recent advances in the size and power of digital chips and digital storage media have made the invention described herein practical in that large amounts of digital data, which would provide for storing meaningful and practical medical information, can be stored on miniature chips and media that are lightweight, compact and would lend themselves to easy storage and retrieval in an emergency situation. Also, in the invention described herein, the digital storage media would not require electrical power and therefore a battery would not be required which would further reduce weight and increase portability. Advances in Internet speed and accessibility would also make it advantageous to link the bodily worn device to a central website via a unique user code so as to augment the digital storage capacity of the storage device and provide for international accessibility of user medical records and information in an emergency.

Also, combined as an integral part of this invention is a base unit and/or module which can be used in conjunction with the device to access, capture or otherwise obtain the stored information from the device in a non-contact wireless method as described herein. The preferred configuration of the module is a wireless and non contact means of accessing the stored data (induction, electromagnetic or radio transmitted signal with receiver wand) routing the data from the wand into the module in digital format either with a fiber optic cable, serial or parallel computer cable, or any other appropriate means, then sending the data through an interface circuit which would connect directly to an existing patent monitor or into a personal computer for viewing and interpretation by medical personnel. The prior art in this area of invention and most specifically Eberhardt U.S. Pat. No. 5,659,741; Doue U.S. Pat. No. 5,361,202; Whalen U.S. Pat. No. 5,327,341 fails to each many of the critical and practical new improvements embodied in this invention. Eberhardt's main focus is on a massive central computer system for obtaining and managing medical data. Although Eberhardt briefly mentions storage devices for medical data he fails to teach or disclose any of the improvements embodied in this invention including but not limited to non contact and wireless transfer of data from the storage device to the module via a inductance or differential data transmission, the battery operation of the storage device, the transponder signal emitted from the device as a locator, making the device waterproof, explosion proof etc., for law enforcement and military applications. Eberhardt also fails to teach the preferred embodiment of the base module which would most likely be a simple plus in module to an existing patient monitor to minimize the coast to the health care system. Doue teaches a computer system and software for improving the management of a patient's stay in a hospital but falls to teach or mention the medallion or pendant storage device or any of the aspects of storing and interpreting medical data in an emergency response situation. Whalen, like Doue, teaches a software and computer system for managing patient files and organizing medical records in general terms but does not teach any of the art of the bodily worn storage device, the wireless data retrieval, or the plug in interface module.

BRIEF SUMMARY OF THE INVENTION

The invention disclosed describes a novel new approach to the storage, bodily wearing and retrieval of medical records, emergency medical treatment data, organ donor data, living will data, etc., in a rapid non contact manner, for displaying such data on a patient monitor for rapid emergency medical treatment, personal identification, autopsy, etc. The bodily device can also be linked to the Internet via a user code with would enable the users records to be accessible remotely and to augment the digital storage capacity of said device. The novel improvements of this device also describe a means of camouflaging the device as jewelry or a wristwatch or pocket watch so as to provide a tracking device and improvements to make the device waterproof and explosion proof, so as to be used as digital dogtags for military, law enforcement, or providing a hand held miniature computer type device with display.

The invention described herein has many improvements and innovations over prior art which, in part, include:

a). A large digital storage medium such as a computer chip, flash memory disk or other digital media for storage of large amounts of useful and meaningful medical information and records, including but not limited to pre-existing serious medical conditions, allergies to medications and drugs, ECG records, ex-rays, cardiac images or summaries of serious medical conditions, in the event of a medical emergency.

b). The digital storage of a color photo identification, iris eye scan identifier, fingerprints, dental records, of the wearer of the device to provide a positive identification in the event the wearer is unconscious or dead as a result of a medical emergency.

c). A decorative and/or functional use of the device such as embodying it into a wristwatch, enclosing the device in a pendant or medallion which is ornamental and resembles fine jewelry, or creating a decorative bracelet or other such device, but at the same time has the characteristics of being waterproof, explosion proof and bullet proof in the event the device is used as a digital dogtag for military applications or law enforcement or in the event the wearer is in a catastrophic accident such as a plane crash, train wreck, etc., wear body identification becomes an extremely difficult or near impossible task due to little or no remains of the victims body. There are many cases in aircraft accidents and in combat where the human body is literally blown into thousand of small and untraceable pieces and the medallion or digital dogtag could provide a means of identification and provide a clue to the fate of a relative or loved one to provide physiological closure.

d). Providing a rapid means of accessing the digital storage media for updating the information, retrieving the information in the event of an emergency. Such retrieval means could include a laser scanner head, a serial or parallel computer port, a digital phono jack, wireless AM or FM transmission, or fiber optic transmission, bar code scanner, inductive wand scanner or any other rapid and appropriate digital means to retrieve the data in the event of an emergency. The device can also be linked via a unique user serial number to a central website via the Internet. Such an Internet link can improve remote accessibility on an international scale as well as augment the digital storage capacity of the device via remote server and storage devices. The preferred access means embodied in this device is the electromagnetic wand or inductance wand which affords a rapid and convenient means of accessing the device data without any physical contact with the device or having to hook up any leads, wires or to insert the device in any slot, computer reader, disk reader, etc., which has been described by prior art.

e). Providing a battery pack or DC battery for long term electrical power of the device in the event it is embodied into a digital wristwatch, for the powering of AM or FM digital data transmission of stored information, for powering an AM or FM transponder signal in the event the wearer is lost due to Alzheimer's disease, dementia, or hurt in an accident so as to track the wearer and locate their position using a Global Positioning System type network or local tracking network.

f). Providing a base unit for retrieving the data in an emergency such as in an ambulance, software and a computer screen for viewing the medical information and a means of transmitting the data via AM, FM, telemetry or digital telephone lines from the emergency vehicle to a hospital emergency room in the event of a medical emergency. The form of the base unit would most conveniently be in the form of a portable computer, dedicated hand held display and transmitter unit or could be in the form of a personal computer, but not need to be. It is most likely that, given the present state of medicine and the drive to reduce cost, the based unit will be no more than an interface module, which will consist of a printed circuit board and A/D converter which would plug into an existing patient monitor mounted in an ambulance or in an emergency room or physician's office and such monitoring device performs a plurality of physiological function monitoring including ECG, blood gas, heart rate, respiration, etc., and the device digital information would be dumped into such a monitor and displayed on a split screen format for emergency medical treatment. It would be advantageous for each display computer to have Internet access to the computer can link to a central website where user records can also be accessed using a secure password code which is affixed to the bodily worn device.

g). Providing an AM or FM transponder signal which is emitted from the device to act as a tracking device in the event the wearer is in a remote location and has an accident, if the wearer wanders off due to dementia, Alzheimer's disease, old age or is stricken with illness and needs to be located. Or, in the case of military applications or law enforcement officers to track and locate wounded, dead, lost or captured soldiers, sailors, or airmen or law enforcement officers. This invention, when worn by a child in the form of a watch or pendant, could also be used as a child protection tracking device in the event a child wandered off, was kidnapped or taken against their will in a nasty divorce. Since the device would look like a piece of jewelry, the person taking the child would not know the child was wearing a tracking device.

h). Providing a waterproof, explosion proof and bullet proof shell or casing around the inner workings and storage device to protect it in the event of a catastrophic accident or military disaster or combat.

i). Provide a clear and standard identification symbol on the exterior of the device identifying it as a medical and/or identification digital storage device and which identification symbol is further used to categorize the device into a series of classes, for easy visual recognition, such as green for non-life threatening medical conditions or normal conditions, yellow for mild to moderate medical conditions or drug interactions or red for serious or severe medical conditions which would be life threatening. The classification could also be done with symbols or alpha numerical code or classes of which bar coding or any other appropriate means.

BRIEF DESCRIPTION OF THE DRAWINGS

FIG. 1B also indicates the markings color coding or other alpha-numeric coding which would identify the class of severity of the medical defect of the wearer on the exterior of the shell. FIG. 1B also shows an internal printed circuit board mounted in a specially designed shock resistant groove. Such printed circuit board would hold a long life lithium battery or equivalent, digital storage media, radio signal transponder, optical scanner head (optional), digital or analog wire jack (optional). FIG. 1B also shows the exterior rim of the outer shell being welded or hermetically sealed to prevent any tampering or unauthorized opening of the device. The back exterior of the shell also could have a bar code identification number to signify manufacturers lot code, confidential wearer ID number or any other variety of encoded identification information which has utility for either emergencies or routine service and maintenance of the device. FIG. 1B also indicates the shell of the device, being of a conductive metal or composite material, can act as an electrode in the event the manufacturer chooses to use this method as a means of transmitting the data via an intimate contact probe between the device and the base unit.

FIG. 1A shows a front cut away view of the bodily worn device with its main components mounted to a printed circuit board of an equivalent device. This figure shows a long life battery which can be replaced or recharged, if required, a transmitter/receiver transponder unit, a digital media storage device, an optical eye for transmitting data via a wireless wand, and an optional jack connection for plug-in transmittals and service. Again, either an optional time piece watch or jewelry can be mounted on the front of the device to make it more attractive and decorative.

FIG. 5 can also be referenced to show a practical graphic representation of the figure two block diagram. The bodily worn device 27 stores medical records and personal information of the user. These records and personal information can be accessed using either the interface unit and scanning wand 26 so to be displayed on portable field unit 25 or base unit 24. As an additional and/or alternative means of storing and accessing said user records a serial number is inputted into a central website via access to the Internet through either the base unit 24 or field unit 25, the user records are accessible via this Internet link without having to use the interface wand to retrieve the records from within the bodily device. This Internet link can greatly augment the storage capacity of medical records and data available to a user in an emergency and can provide an international network to access said records in an emergency when on vacation or travel.

FIG. 4B shows a front view of the tag embodiment and various means of mounting the device on either a necklace, bracelet, or simply carrying the tag in a persons pocket or wallet. The tag can be coded with any type of previously described color or alpha numeric codes to signify the severity of the persons medical deficiency. Also, any type of decorative finish can be added to the exterior to make the device more attractive to the consumer and on the contrary the device can be left plain and uniform for law enforcement, military and fire fighting personnel.

The data is organized into a series of pages in the storage system for ease of use and to make the data medically significant to medical personnel.

Figure 7:
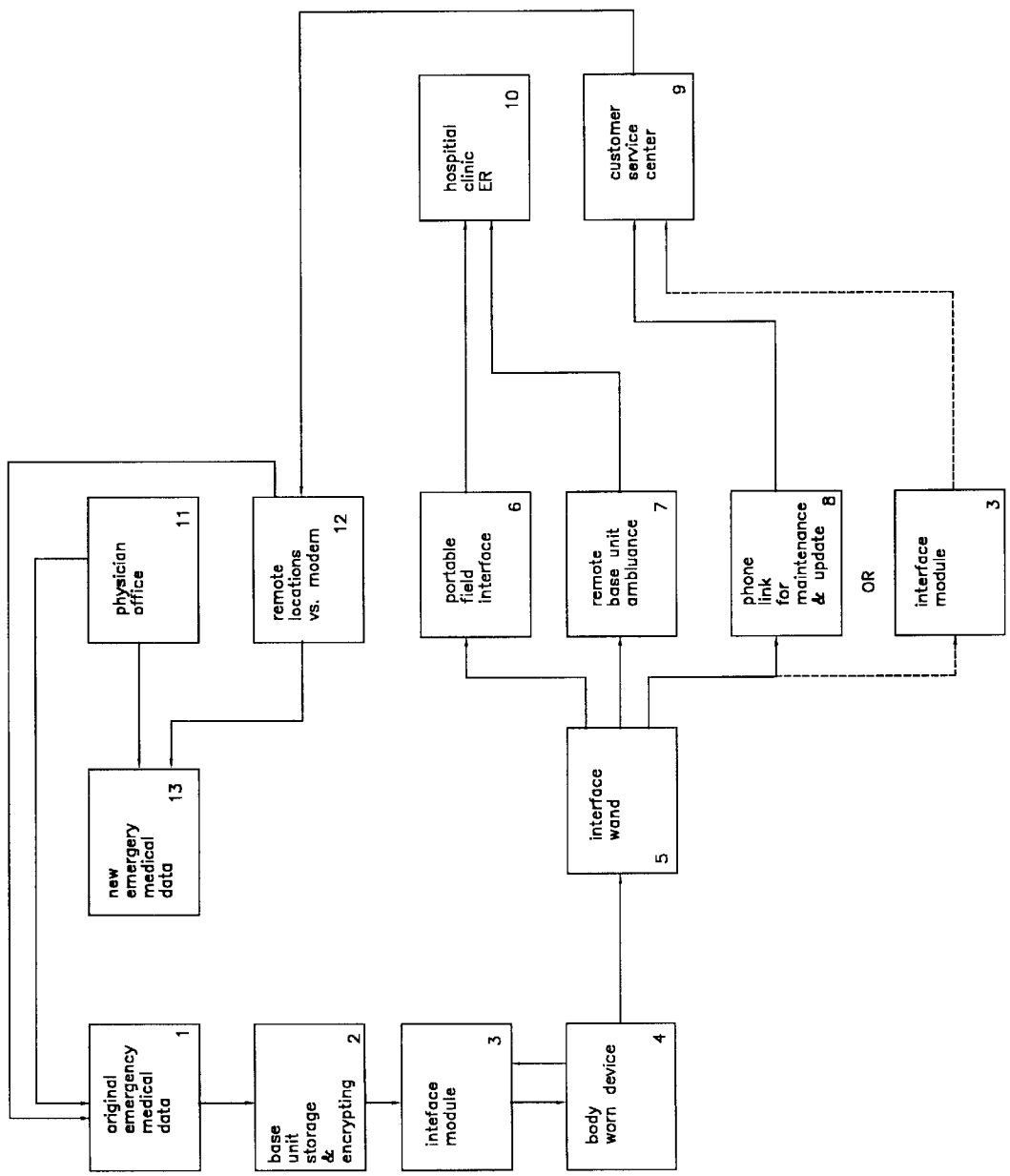

FIG. 7 shows one embodiment of the flow of data and the software logic which would be used to control all of the data storage functions and transmittal functions of the entire hardware and electronics systems described.

Figure 8:
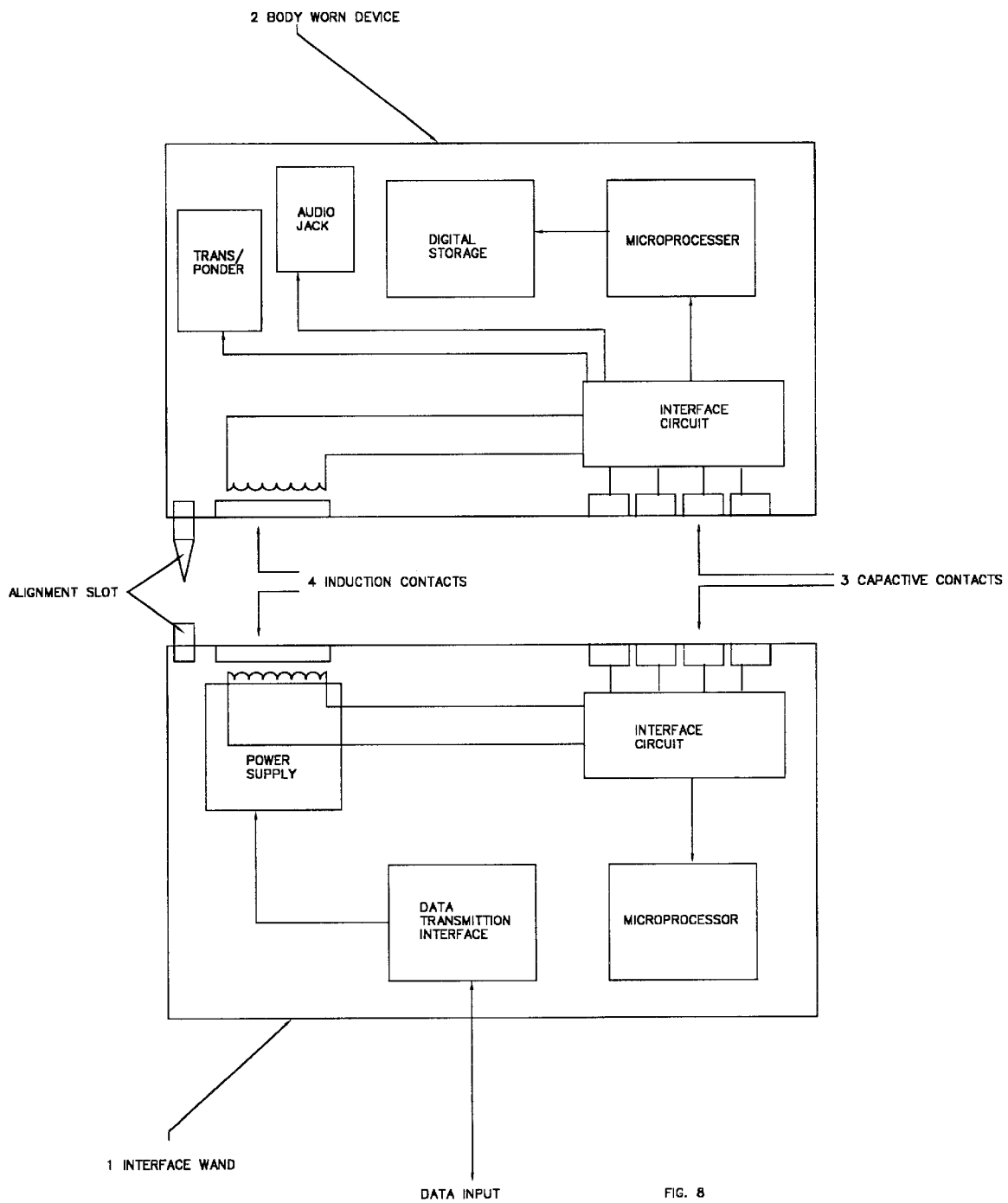

FIG. 8 shows one typical embodiment of the means to mechanically align the interface wand and the Bodily worn device to power the BWD as well as retrieve and transmit data to the device.

FIG. 9 shows one typical means of organizing the electronics of the device, distribution of electrical power, and control software of the device. The organization of electronics is done in such a way, in part, as to isolate the electrical power circuits from communications circuits to avoid RF interference.

DETAILED DESCRIPTION OF THE INVENTION

The invention disclosed herein is an improved method of storing and retrieving digitized medical records which are stored in a protective bodily worn enclosure. The inventor has done several thorough patent searches and finds no other prior art which describes such a digital device(s) and teaches its patentable features.

Figure 1:
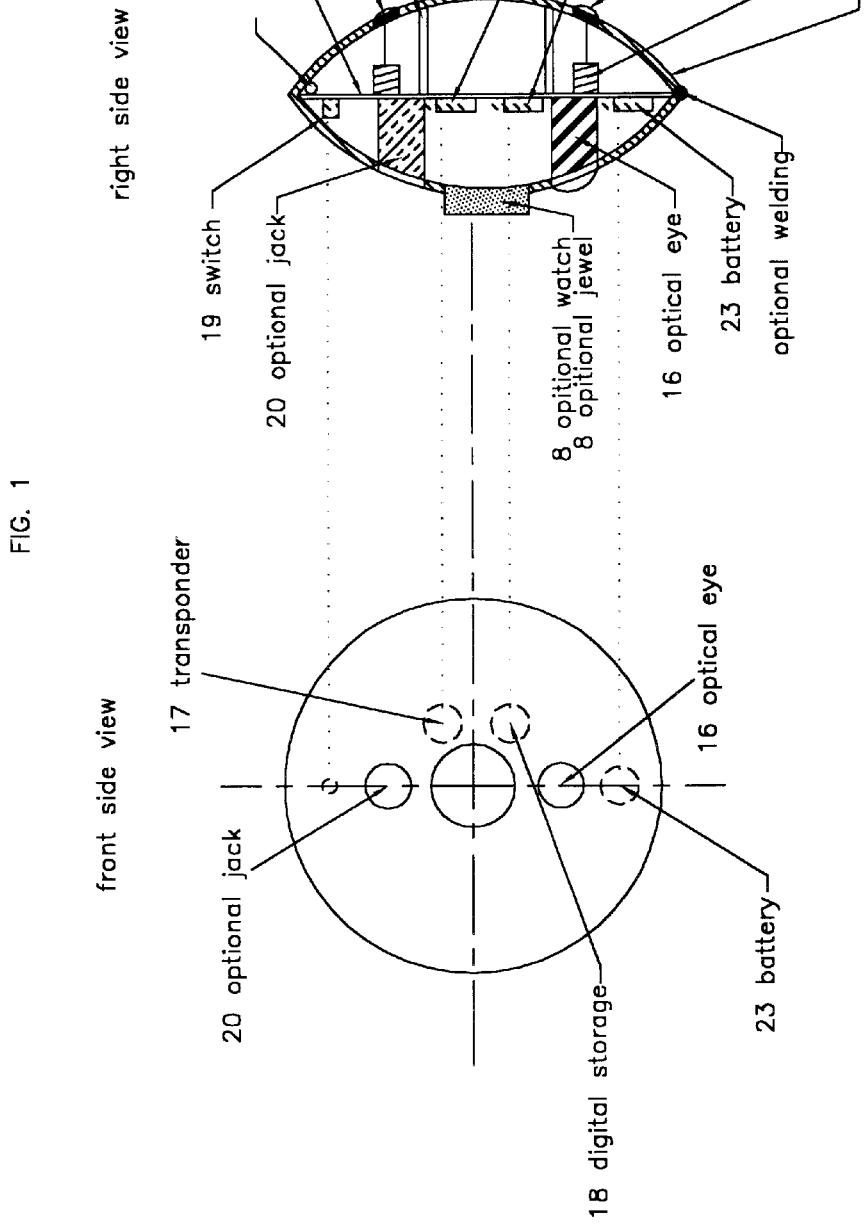
FIG. 1A outlines one embodiment of the bodily worn device in the form of a medallion or locket which could also include a small watch in the front or jewelry for decorative purposes.
FIG. 1B shows a cross sectional view of the device which includes a clam shell-like casing made of polished titanium, stainless steel or an appropriate strength composite or polymer material which would withstand severe underwater pressure, explosions and/or fragments or bullets. Also shown in FIG. 1A is an "O" ring groove seal, and a polymer "O" ring, and an appropriate equivalent which would seal the case from water, dust, etc., and such "O" ring would be sealed with a graphite dust or equivalent material, naked to the human eye, which would provide any indication if the device was opened and or tampered with by an unauthorized person.

Reference to FIG. 1

One embodiment of the invention is shown in FIGS. 1(A & B). The device has an outer protective shell 1 which is made from either steel, titanium, aluminum or a conductive polymer, or another appropriately strong, but light-weight conductive material which can be polished to an aesthetic finish. In one embodiment of the invention the shell is conductive so as to act as an antenna for the AM or FM transponder unit 5 which is embodied in the device for tracking or locating the wearer and in this embodiment an anti Radio Frequency (RF) film coating 2 is placed on the inside of the shell to protect the devices electronics from RF interference from ambient sources. In another embodiment of the invention wherein a transponder is not used shell 1 can be non-conductive to avoid RF interference and is also shielded from radio frequency with coating 2. Shell 1 is designed with an appropriate groove and/or recess in its outside front to accommodate either a watch, jewelry or other ornamental or functional objects. Shell 1 is designed in such fashion to either include an internal "O" ring groove 3 or polymer "O" ring 4 for the purpose of waterproof sealing of the two halves of shell 1. Included on one embodiment of the invention would be a means of locking or fastening the halves of the shell 1 closed which could include miniature screws 5 with internal standoffs 6 as shown, a press fit between the two halves of shell 1 such that the halves are intimately locked together yet can be opened if required, or an external lock and clasp assembly 7 shown which is similar to a locket or pocket watch. In another embodiment of the invention the halves of shell 1 can be welded together around the perimeter or glued along the inner perimeter so as to provide for a waterproof and tamper proof seal to the shell 1. The outside of shell 1 is marked with appropriate symbols 8 which identify the device as a medical information device and an alpha numerical code or color code 9 which identifies the level of severity of the preexisting medical condition of the wearer. The device can be worn on the exterior of the body by means of a bracelet or necklace 12 or any other appropriate means of affixing the device to the body where it is clearly visible and readily accessible in an emergency. In one embodiment mounted to one interior halve of shell 1 is a series of threaded standoffs 13 upon which is mounted Printed Circuit Board 14 which holds the main electronic circuits and components. An alternative mounting of PC Board 14 is a groove which is machined in the inner perimeter of one half of shell 1 and acts to nest the pc board in place. In such a configuration a polymer pad 15 can be placed in between shell 1 and pc board 14 so as to act as a shock absorber or dampened so as to mechanically isolate pc board 14 from exterior vibrations or shocks. Another embodiment of the shock absorber concept is to fill the entire shell 1 with a non-conductive insulation polymer once all electronics and components are in place in shell 1 so as to provide a mechanical damping nest for all interior components. Mounted to the printed circuit board are a series of electrical components and interconnecting electrical circuitry for the device. One such component is an optical reading eye 16 with is mounted to the pc circuitry. An aperture opening in shell 1 allows the optical eye to protrude throughout the shell so as to be read by an optical reading device which is further described in this invention. The optical eye 16 is one such way in which the stored digital medical data is retrieved from the device in a rapid wireless fashion. A transponder 17 is mounted to pc board 14 and acts to emit either an AM or FM signal from the device in the event the wearer is lost, kidnapped or incapacitated or otherwise needs to be located. A digital storage media 18 is mounted to the pc board 14 and is used to store all of the wearer's medical records and data as described herein. The circuitry of the pc board is designed in such a way so as to provide for rapid means of accessing the digital data from the storage media 18 via the optical eye 16 through a switching components 19. The switching component, mounted to the pc board 14, is of such a variety as to allow for two way transmission of data to and from the storage media 18. The storage media 18 is such a variety so as to be both written on and read, but, for security reasons can only be written on by a person that knows confidential passwords and/or messages as to protect the integrity of the device and the medical data stored in media 18. A long life battery 19 of the type which is commonly used in watches and other low energy usage devices is mounted in pc board 14 and acts to provide dc low amperage electrical power to the transponder and any other components which from time to time may require power for the operation of the device. In general, the device has been designed so as to be a passive device which means under normal circumstances it is not using power and thus conserves the energy in the battery for emergency situations. A miniature jack 20 is mounted to the pc board 14 and is used to provide an alternative means of hard wire connecting the device to a base unit, patient monitor or other device for displaying the stored medical data on a display screen. The jack can be of any appropriate type such as a phono jack, serial or parallel jack, cable jack or any other appropriate miniature type jack for uni or bi-directional transmission of data. Alternatives to the optical eye 16 for retrieving the digital data could include capacitive probes 21 mounted on the BWD and the interface wand, a bar code reading device, a telemetric transmission device of other wireless, low energy means of transmitting and receiving digital data. An important alternative to the long life battery included in the device shown herein is an electromagnetic means of powering the device from the interface wand to the BWD by mounting inductive windings of a transformer 22 on both the wand and the BWD. Primary coils of an inductive transformer can be mounted on the wand and secondary coils can be mounted on the BWD.

When the inductive pads of the wand and BWD are in close proximity enough voltage and electrical power is transferred to operated the BWD during data transmission and can also be used to recharge on the board battery 19.

Figure 2:
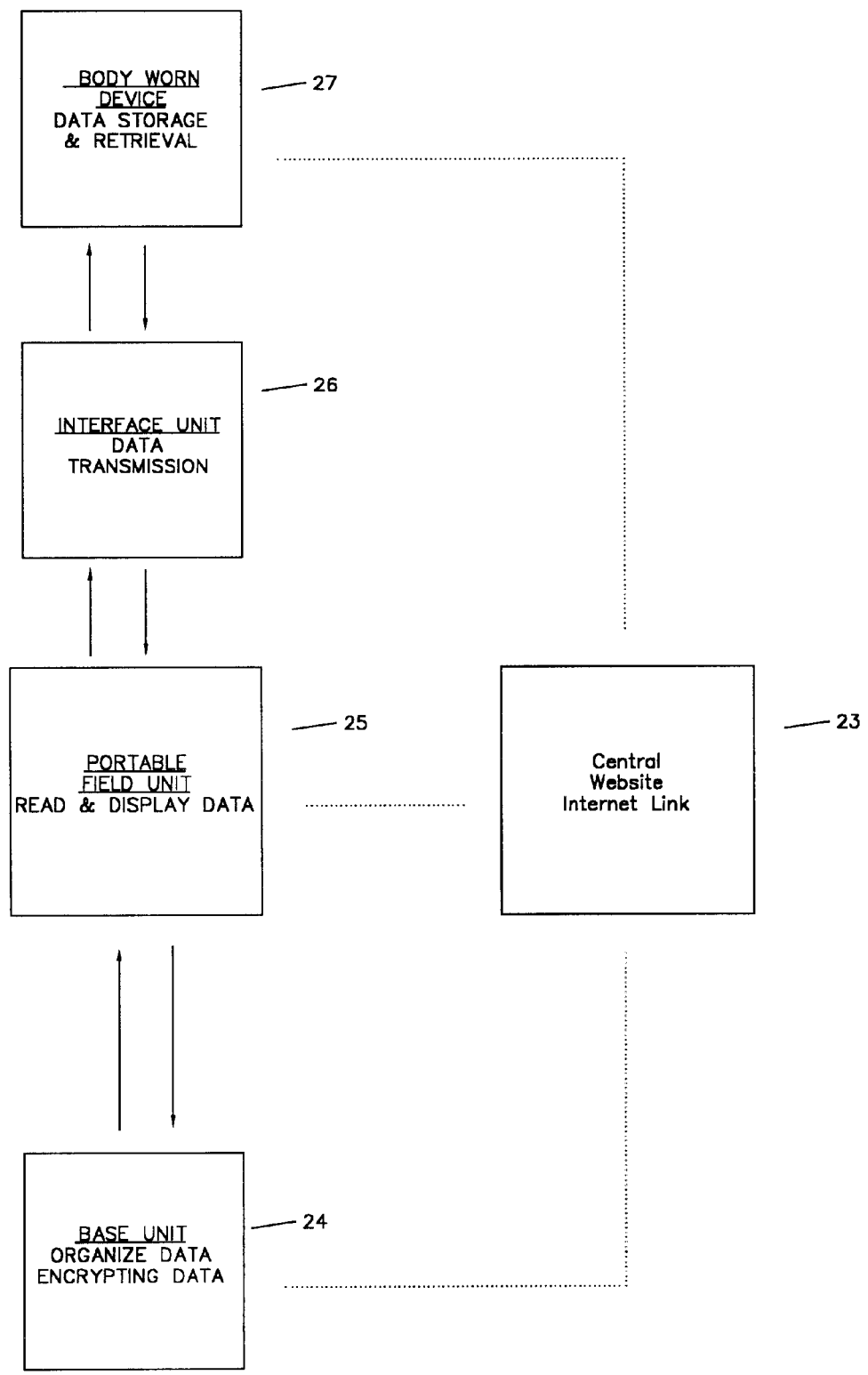
FIG. 2 shows a block diagram of a preferred embodiment of the data flow and communications of the various hardware and telecommunications components of the overall system described herein.
Figure 4A:
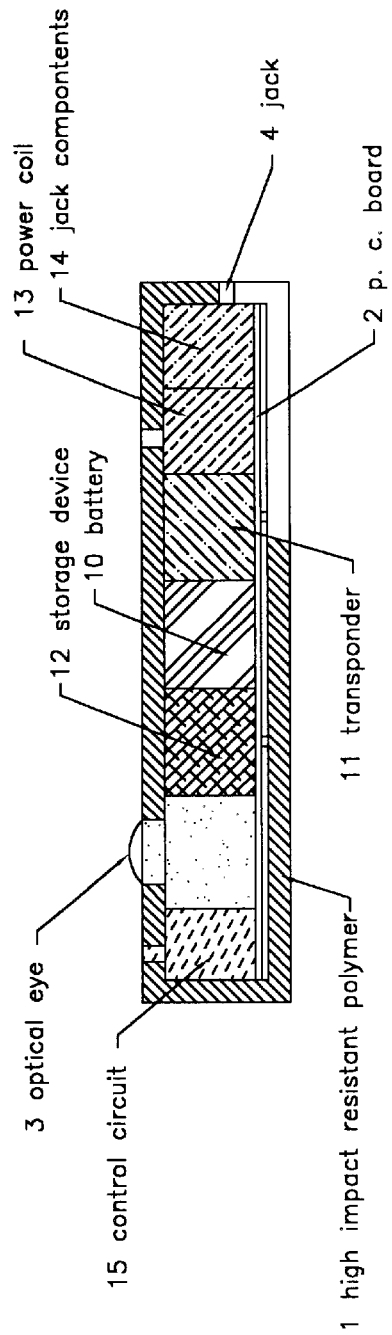
FIG. 4A shows the device as embodied in the form of a tag which can be worn either around the neck and a digital "dogtag" or can be worn on a bracelet to be carried in a pocket, etc. The tag as show in FIG. 4A can be made from a molded fire and impact resistant polymer and the electronic components can be molded into the polymer tag by heating the polymer or having the polymer be a two part type epoxy whereby when the parts are mixed they solidify and harden.
Figure 4B:
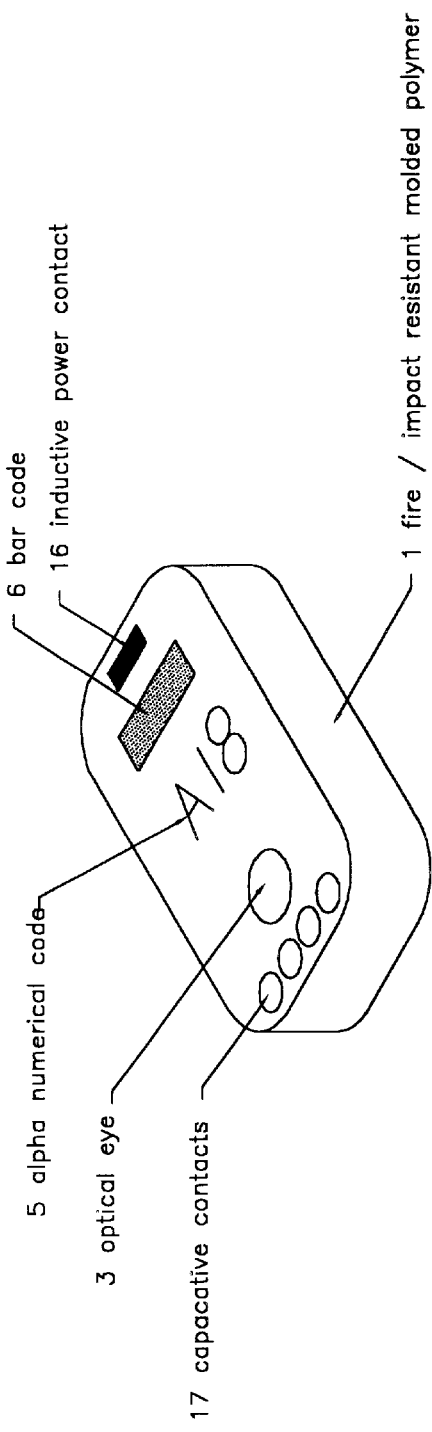
FIG. 4B shows a cross section of the tag embodiment. Molded into the tag is a miniature battery pack which can be accessed to replace or recharge batteries, a digital storage chip or other appropriate media, a transponder receiver/transmitter for tracking the wearer of the device, an optical scanner eye, or other appropriate access means, a hard wire jack access which can be in the form of a miniature computer cable connection or other appropriate means, a bar code strip to provide quick access to tag serial number and other identification data. The components are to be molded and imbedded below the surface of the tag so as to provide for integral means of waterproofing the function of the device, allowing the device to be shock resistant, fire resistant and explosion resistant.

Reference to FIG. 2 (See FIGS. 4(A & B))

Figure 5A:
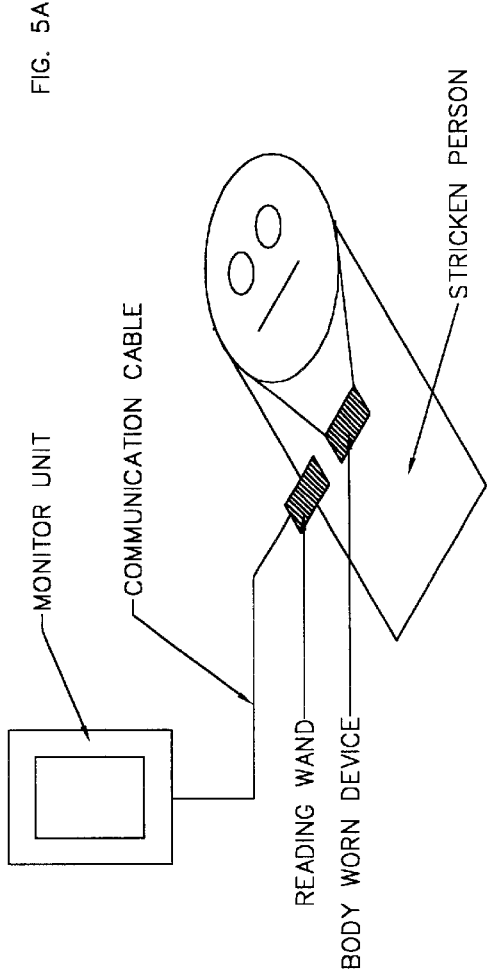
FIG. 5A shows the preferred embodiment of the bodily worn device and the base unit which would be used to access the digital data in a rapid, wireless manner. As shown, an incapacitated person wearing the bodily worn device (BWD) can have their personal medical records accessed in an emergency situation by the EMT holding the inductance, electromagnetic or other type of non-contact wand.
Figure 5B:
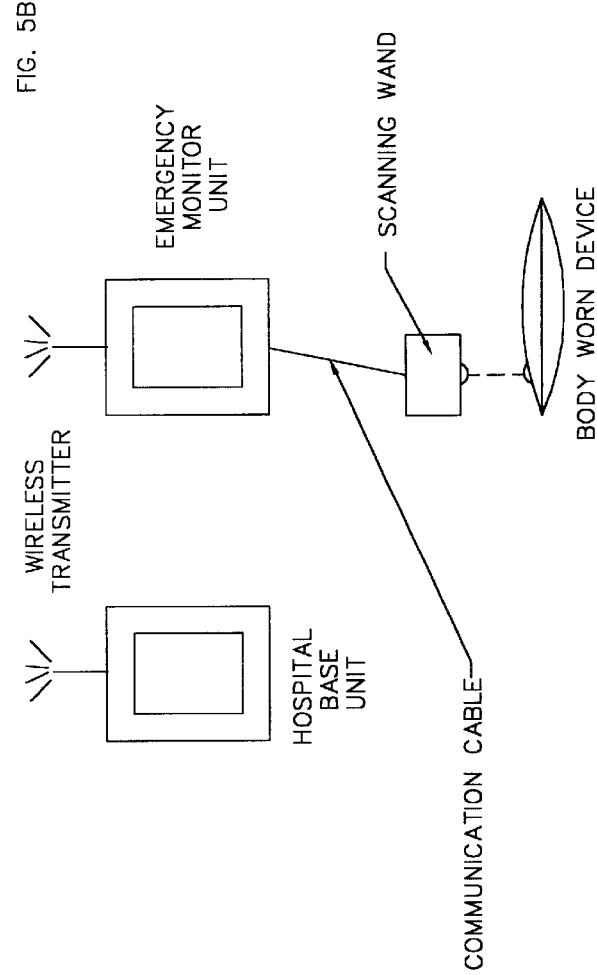
FIG. 5B shows one embodiment of a system to retrieve data from the Bodily worn device via the scanning wand. The data is stored in the Emergency Monitor Unit and can be sent via wireless means to the Hospital Base Unit.

FIG. 2 shows a block diagram of a preferred embodiment of the data flow and communications of the various hardware and telecommunications components of the overall system described herein. FIG. 5 can also be referenced to show a practical graphic representation of the figure two block diagram. The bodily worn device 27 stores medical records and personal information of the user within the device. The same patient records can be also stored remotely in a central database and accessed via the central website and Internet Link 23 when used in conjunction with the portable field unit 25 or base unit 24. A user's records and personal information can be accessed from the bodily worn device 27 using the interface unit and scanning wand 26 so to be displayed on portable field unit 25 or base unit 24. Each bodily worn device 27 contains a digital serial number which is stored within the memory storage device. This serial number is automatically recognized by the interface wand and system software so as to provide system security and confidentiality of patient records. A non-system reader wand would not be able to access and read the user serial number and patient records. Addition security features include data encryption of the serial number and patient records. As an additional and/or alternative means of storing and accessing said user records a separate user serial number is displayed on the exterior of the bodily worn device. In an emergency this visible serial number is inputted into the systems central website, via access to the Internet through either the base unit 24 or field unit 25, and the user records are accessible via this Internet link without having to use the interface wand to retrieve the records from within the bodily device. Access to the website and patient database is limited to medical personnel via a separate medical access code which acts as a second and redundant password to prevent unauthorized personnel from accessing the remote website database. This Internet link greatly augments the storage capacity of medical records (only limited by the number of servers and back end computers in the central website system) and data available to a user in an emergency and can provide an international network to access said records in an emergency when on vacation or travel. In an emergency a medical service provider would have a choice of either accessing medical records from a portable field unit 25 or base unit 24 via either the interface unit and wand 26 or the central website 23. If a medical provide did not have access to the interface wand hardware then they could use the website connection to access user records.

Figure 3:
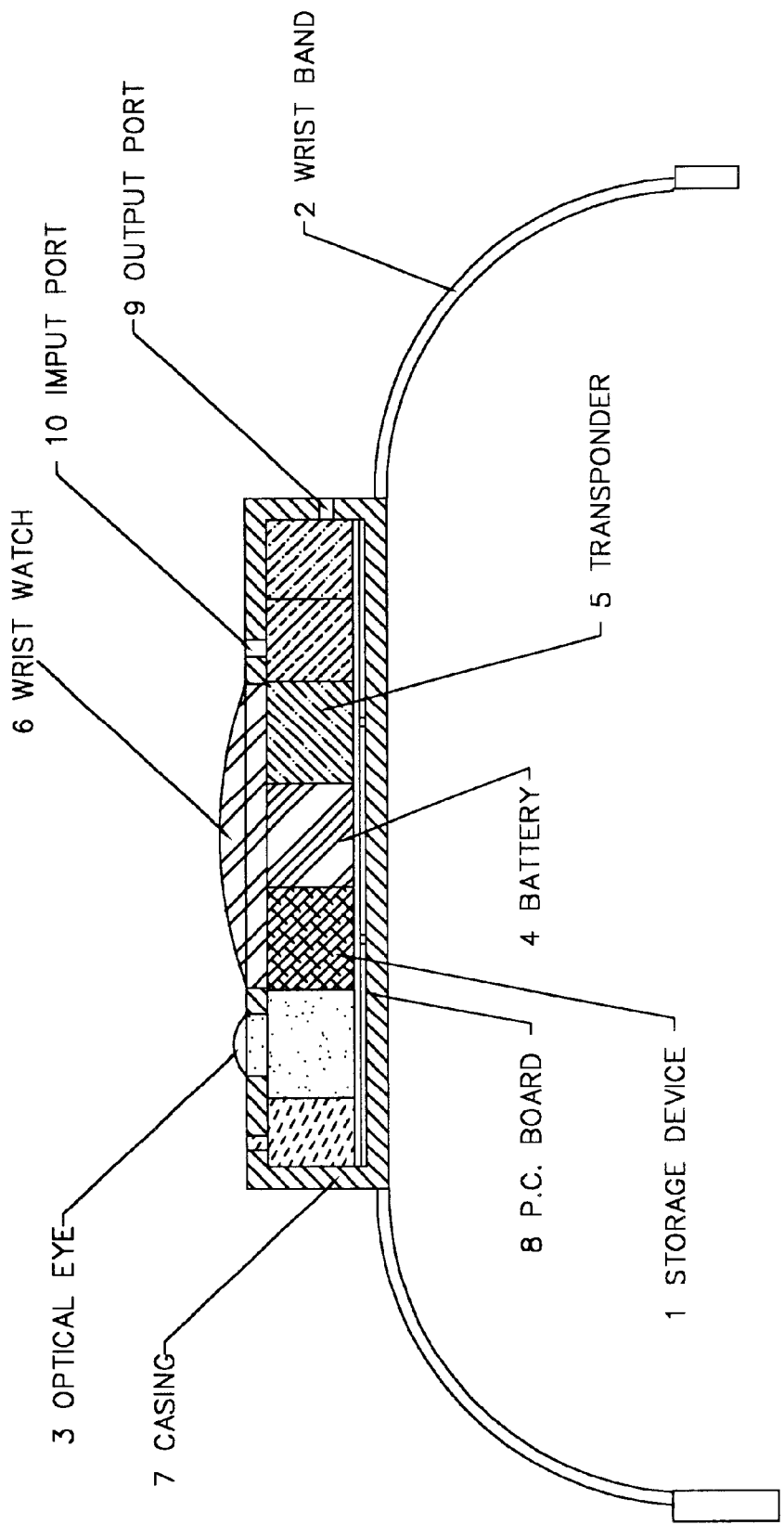
FIG. 3 shows a cross section of the device as embodied in a watch or ring. Again the device is miniaturized to such a small size as to make it feasible to be included in a wristwatch or ring. The same features and criterion embodied in FIGS. 1(A & B) and FIGS. 4(A & B) apply to FIG. 3, e.g., battery unit, optical eye, transponder, digital storage, etc.

Reference to FIGS. 3(A & B)

FIGS. 3(A & B ) shows the wrist watch embodiment of the Bodily worn device in a cut-away drawing. The rugged, waterproof and shock resistant casing 7 is mounted to the wristband 2 using a suitable means for ensuring mechanical bonding, including molding, gluing, or running the band 2 through a slot in the back of case 7. Optical eye 3 protrudes out of a port which is either machined or molded into the case 7. The hardware and electronics of the optical eye 3 are kept within the case 7 in order to protect them from the elements and damage and are mounted to the pc board 8 so as to complete an electrical circuit with the other components of the device. Battery 4 is mounted onto the printed circuit board 8 using appropriate hardware. The battery can be either a replaceable type or a rechargeable type battery. An access port in the rear of the case 7 would allow for the removal and replacement of the battery and for other maintenance of the device. Transponder 5 is mounted to the pc board 8. Transponder 5 transmits/emits a continuous radio frequency signal which would allow the wearer of the wrist watch device to be located by emergency personnel, rescue workers or law enforcement personnel in the event the wearer is lost, disabled, diseased, or incapacitated in any way. The storage device 1 is mounted to the pc board 8 and is comprised of any suitable digital storage media which can be a digital storage computer chip, a silicon type storage device, flash memory chip or other suitable device. The storage device 1 is connected to an electronic circuit on the pc board 8 which allows the storage device 1 to transmit and receive digital medical records either via to optical eye 3 or the data input port 10 or the data export port 9. The data input port 10 has a digital data jack which protrudes through the case 7 and allows a user to connect a jack or other suitable device to the wrist watch as an alternative means of inputting and storing digital medical records into the device via the electronic circuit imbedded in the pc board 8 which connects the surface mounted devices, including the input port 10 and the storage device 1. The output port 9 allows an emergency medical technician or other person who wishes to access the stored digital information to retrieve said digital records by plugging a jack or other hard connection means into the port 9. This is an alternative to the wireless data transmission via the optical eye 3. The wrist watch 6 is a time piece which allows the overall device to serve another useful purpose as well as to be stylish and cosmetically appealing for the wearer of the device.

Reference to FIGS. 4(A & B)

FIGS. 4(A & B) shows another embodiment of the invention disclosed herein. As previously described FIGS. 4(A & B) shows a version of the invention which broadly comprises the electronic inner workings of the device molded within a rigid polymer enclosure which is shock proof, water proof, explosion and fire resistant. This embodiment of the invention can be either in the form of a digital dogtag, pendant or bracelet worn tag. Polymer shell 1 is molded around the inner electronics and board 2 in such a fashion that the seals around the protruding optical eye 3 and communications jack 4 are water tight and hermetically sealed and the entire body of the polymer shell 1 is water tight and hermetically sealed. The exterior of the shell 1 is color coded or alpha numeric coded 5 in such a way as to identify the severity of a pre-existing medical condition of the wearer. A bar code 6 on the exterior of the shell 1 can be used to store either identifier code numbers, manufacturers lot code numbers or any other alpha numerical identification code. Printed circuit pc board 7 is designed in such a way that all of the main components are surface mounted and oriented either toward the front or back of the device as required. Optical scanning eye 8 is oriented and mounted so that the optical eye protrudes through the outer shell 1 for rapid wireless reading of stored digital data. Communications port/jack 9 protrudes the outer shell 1 so as to provide for a back up hard wired means of communicating with the device and transmitting digital data. A long life cadmium batter 10, either rechargeable or permanent life, is mounted to the pc board and can be either permanently sealed by shell 1 or have a removable access panel for changing of the battery when required.

This FIGS. 4(A & B) embodiment of the invention has all of the other components listed and described in FIGS. 1(A & B) which include the optical eye, transponder, long life battery, digital storage and retrieval device, two way data transfer switch, pc board, shell, etc. The embodiments and the components function the same way as the prior embodiment. The obvious difference between the FIGS. 1(A & B) and FIGS. 4(A & B) is the FIGS. 4(A & B) has molded polymer shell, which can be in the form of either a tag, round pendant, bracelet tag or any other practical and functional shape. The molded shell acts to seal the electronic working of the device in such a way as to be waterproof, fire resistant, shock and explosion resistant so as to make the FIGS. 4(A & B) embodiment practical for military, fire fighters and law enforcement applications.

The transponder 11 is mounted to the pc board 7 and emits a radio frequency signal which is used by emergency personnel, military personnel or others to find the wearer of the device if the wearer is dead, injured or incapacitated and requires assistance. The storage device 12 is mounted to the pc board 7 and is connected via an electrical circuit mounted on the pc board 7 to the other electronic devices mounted on the pc board 7 to receive and transmit digital data as well as other functions described herein. The storage device 12 can be either a computer chip storage device, flash memory chip or other suitable high capacity digital memory storage device. The power coil 13 with its inductive power contact allows the device to receive electrical power, as an option to the on board battery, by mating said 30 power contacts with a remote device which contains the opposite side and mating coils to the inductive coil. Electrical current can then be transmitted across the inductive contact to the device via the completion of the inductive coil connection. The jack component 14 allows for remote access to the digital data by plugging in a male jack to the female jack receptacle. The jack can be any type of standard miniature electronic jack and can be used to transmit digital data to the device as well as receive digital data from the device for viewing in an emergency. The control circuit 15 can be comprised of a digital logic chip or other suitable device which allows for the storage of logic software which can control the functions of the device. Such functions would be the organization of the digital medical records into page format, ensuring the battery 10 has a proper charge to maintain functions of the device (an audible signal can be emitted if the battery is getting low), allow for orderly updating of the digital medical records via the input/output device 14 or optical eye 3, ensure that the device was not over powered via the power coil 13, sense that the transponder 11 was properly functioning and emitting its proper radio frequency signal, as well as other control and logic functions of the device further described in FIG. 7.

Reference to FIGS. 5(A & B)

The bodily worn digital storage device in its embodiments described herein is used with other complimentary devices patented by this inventor. The other integral components of an overall system for using the Bodily Worn Device in a practical situation are shown in various configurations in FIGS. 5(A & B). The complimentary components include:

a). A portable or remote display unit with an optical reading wand, used by EMT's, paramedics or corpsmen, allows for rapid retrieval and display of vital medical and identification records in remote locations.

b). Included with the portable or remote unit is the capability of sending the information wireless either using AM, FM or telemetry technology.

c). Also shown is a module which can be added to a more substantial patient monitoring base unit used by either an ambulance or emergency room. The purpose of the module is to reduce the overall cost of integrating this technology into existing patient monitoring equipment presenting used in medicine today.

d). Included with either the portable unit, module unit or base unit is a wireless means of retrieving data and/or transmitting and updating data back to the Bodily Worn Device. This wireless means could include optical scanning differential data transmission, AM or FM wireless transmission or any other form of practical wireless transmission presently in use or to be conceived.

Figure 6:
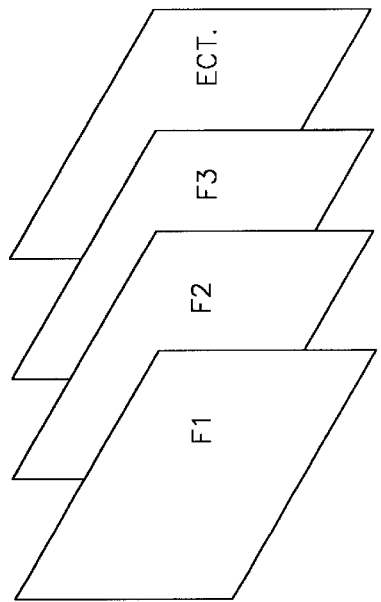
FIG. 6 shows one typical embodiment of the organization of the medical records into digital "pages which can be prioritized in a means so that critical medical data is displayed in first order and secondary data is then available.

11. Reference to FIGS. 6 and 7

An integral part of the invention disclosed herein is the software invented to store the digitized medical records in orderly files, locate and retrieve the digital records in rapid wireless fashion, allow for two way transmission of data so stored records can be periodically updated as well as retrieved, display the digital records on the module or portable screen in an orderly and easily readable standard fashion.

FIG. 6 shows one possible such embodiment of the standard format for the medical records organization in digital files or display screen "pages". When the digital records are retrieved and displayed through either the module unit, portable display unit or base unit previously mentioned, they will appear as either one organized page or in a series of organized pages as shown in FIG. 6. The main page of the records will show, starting from the upper left hand corner of the display page:

a). Either color or black and white photo of the wearer of the device.

b). A thumb print, iris print of other distinguishing physical characteristic.

c). Dental records.

d). Sample ECG or Cardiac Echo Scan.

e). A section of "Emergency Medical Data" which could include:
  1). blood type
  2). present medication being taken
  3). drug interaction precautions
  4). drug and/or allergic reaction precautions
  5). a description of serious preexisting medical conditions f). A section for Emergency Medical Instructions, which could include:
  1). administering of certain suggested drugs or physical treatments
  2). calling emergency physician numbers listed
  3). bringing the patient to a certain type of clinic or facility based on religious beliefs, etc.
  4). living will instructions in the case of seriously ill patients g). Organ Donor instruction.

h). Living Will instructions which could include:
  1). instructions for life support or termination of treatment
  2). notification of next of kin and/or friends including addresses and telephone numbers On subsequent pages other types of supporting medical records and diagnostic aids could be included, including but not limited to:

a). complete ECG trace b). Cardiac Echo Scan c). EEG trace e). diabetes test results and instructions f). x-ray scans g). etc.

Other pertinent medical records and scans could be included which are tailored to a wearer's specific preexisting medical condition.

12. Reference to FIG. 7

An integral part of the invention disclosed herein is the unique software invented and used as part of the Bodily Worn Device as well as for the module, base unit and a computer system used for organizing and storing large amount of data.

As seen from FIG. 6 the Bodily Worn Device contains important software for the organization and storage of the wearer's medical records and ID information. There is also software integral for the retrieval, management and updating of the Bodily Worn Devices which is contained in the interface module, base unit and central computer system. This additional software is vital to the use and management of the records stored in the Bodily Worn Devices and acts to link all of the components together to act as a total functioning system.

The following is a basic description of the software and its basic functions as depicted in FIG. 7 flowchart. To start the process new/original medical information is organized and edited to fit into the BWD page format either in physicians office or by a third party with access to a patient's medical records using the base unit storage and encrypting software 2 which can be stored in a normal pc or other compatible computer device. One important aspect of this base unit software 2 is the fact that it is capable of encrypting the records so as to be secure and confidential and only accessible to authorized individuals with compatible de-encrypting software. The interface module 3 is an electronic enclosure designed with a "nest" for sitting the Bodily Worn Device into and using wireless optical or differential data transmission. The interface module 3 is used as a link between the BWD 4 and the base unit 2. Software in the Interface module 3 allows for two way communication and transmission of data to and from the BWD for both inputting medical records into the BWD and for retrieving them for editing and updating purposes. The interface module 2 and base unit 2 are each equipped with software and a telephone modem to allow for remote access to, programming and updating of the BWD stored records in remote locations. (For example: and elderly person with a BWD could have their medical records updated while at home using the interface module 3 in their home communicating with a base unit 2 in a remote location via telephone lines.) Once new/original records are burned into the BWD 4 using the base unit 2 and the interface module 3 the wearer is free to use the BWD and travel and move freely about. In the event the wearer is stricken with an emergency illness a Paramedic, EMT or Emergency Room Technician can use the interface wand 5 in conjunction with either the portable field display 6 or the remote ambulance patient monitor 7 to rapidly retrieve and display the stored medical records in the BWD 4, displaying those records in page format as shown in FIG. 6, and sending those stored medical records, via modem or wireless telemetry to a remote emergency room or physicians office for rapid and life saving medical intervention in a crisis situation. Separately, in a non-emergency fashion, either the phone link Unit 8 or the interface module 3 can be used to access information from the BWD 4 through wand 5 so as to perform periodic maintenance, testing, retrieval and updating of medical records via telephone modem, telemetry, cable link or any other type of wireless or hard wire transmission. When a wearer of a BWD 4 has a change in their medical condition, drug treatment, organ donor instructions or living will instructions they have the choice of either going to their physicians office 11 to have the stored medical data updated through the base unit 2 and interface modem 3 or going through a third party insurance carrier, private service or other company 9 which can send updated data through a remote interface module 3 to update the BWD 4 through a telephone modem or other wired or wireless transmission. All of these devices contain software which is compatible with the other devices mentioned and allow for smooth, fluid encrypting, de-crypting, retrieval and display of medical data in emergency and non-emergency situations.

Reference to FIG. 8

FIG. 8 shows an embodiment of the mechanical interface and electrical circuit interface of the reader/wand 1 and bodily Worn Device 2. This interface between the two devices is an integral part of the invention and its operation when a battery is not included in the BWD 2 and external power is required to operate the BWD. Also, the capacitive probes described herein are an important alternative to the optical eye in transmitting and receiving data to the BWD 2 from the wand 1. A mechanical slot or socket is shown which ensures the wand and BWD are rapidly and easily aligned for proper alignment of the inductive pads (power) and capacitive pads (data transmission). Capacitive pads 3 are used to both transmit and receive data to and from the BWD in bi-directional fashion. The primary coils and inductance pad 3 is mounted into the wand 1 as shown and sends electromagnetic voltage across to the secondary coils and inductive pad 4 mounted into the BWD. Electrical power is distributed to the components on the BWD through the interface circuit. The interface circuit could also contain the means to recharge an on board battery as previously described herein.

Reference FIG. 9

FIG. 9 depicts one typical means of organizing the electronic components of the device and distributing electrical power to the components of the device and for transmitting digital to and from components of the device. In the schematic presented in FIG. 9, which is one of many ways organizing the electronics contemplated by this invention, the data transmission lines 11 (typical) which are from the logic chip 4 in the event that the battery becomes low on power or if the logic chip senses that data stored in the storage media 6 is corrupted or inadvertently erased. depicted by the hashed lines, are kept separate from the electric power lines 10 (typical) so as not to have electrical interference, either IF or electromagnetic, come in contact with and corrupt the digital data information. Electrical power can be supplied to the device via the power contact 1 which complete the circuit between the secondary transformer coils 2 and the primary coils of the interface wand 12 or via long battery life 3. The power is then transmitted to the logic chip 4 which acts to meter and distribute power to the optical eye 7, storage media device 6 and transponder 5. The logic chip 4 is connected to the storage media device 6 and is capable of sensing the flow of digital data to and from the storage media 6, determining the amount of data flowing to the device and preventing overloads, quality checking the data flowing to and from the storage media 6 to ensure the data is not corrupted, contains no electrical or RF interference, and is matched by alpha numerical identifier code to the wearers unique alpha numerical serial number code. The logic chip can also monitor the flow of data so as to prevent two way data flow at the same time over the same circuit. The optical eye 7 is connected to the storage media via two way digital data circuit. This allows for digital data to be send from the optical eye 7 to the storage media 6 to initially create digital data files or to erase and up data new digital files. Stored data files can be retrieved from the storage device 6 via access and transmission through the optical eye 7 to the interface wand optical eye 13. As an alternative to the optical eye 7 the input jack 8 allows digital data to be transmitted into the storage media device via hard wired jack connection to the device. As an alternative to the optical eye 7 the output jack 9 allows stored digital data files to be retrieved from the device. The transponder 5 acts to emit a high frequency signal which allows the wearer or holder of the device to be tracked. The transponder 5 also is capable of emitting an audible error signal, via a logic signal which allows the wearer or holder of the device to be tracked. The transponder 5 also is capable of emitting an audible error signal, via a logic signal from the logic chip 4 in the event that the battery becomes low on power or if the logic chip senses that data stored in the storage media 6 is corrupted or inadvertently erased.

What is claimed:

1. An apparatus for storing and retrieving digital records and data from a device carried or worn on a body of an individual comprising a protective outer shell which is fire proof, shock proof, and water resistant for protecting the electronics and inner mechanisms of the device, and an optical eye capable of writing, erasing and re-writing digital data to the bodily worn device in a wireless, non-contact fashion, and digital storage media enclosed in the device for storing the digital data, and a means of supplying electrical powering to the device using wireless, non contact means, and an electronic transponder which emits a radio or other high frequency signal for tracking and locating the wearer of the device, and an RF antenna, RF computer chip, and RF transmitter and receiver hardware for wireless transmission of data and power signals.

2. The apparatus of claim 1 wherein the outer shell is fire proof, water proof, explosion and bullet proof for the purposes of withstanding military or law enforcement combat, train and aircraft accidents, while protecting the inner workings of the device and allowing the device to continue to operate normally and uninterrupted.

3. The apparatus to claim 2 wherein the protective outer shell is designed to incorporate a ring seal so as to make the device able to be opened for servicing and also make the device waterproof.

4. The apparatus of claim 2 wherein protective outer shell is color coded to designate the severity of the wearers medical condition, the wearers military rank or law enforcement rank to allow a care giver to rapidly assess and provide rapid treatment options for the wearer which are tailored to the emergency.

5. The apparatus of claim 2 wherein the protective outer shell contains an alpha numerical marking which designates the wearer's medical condition, personal identification number, military serial number, law enforcement serial or badge number for rapid identification and assessment of the wearer.

6. The apparatus of claim 2 wherein the protective outer shell contains a bar code strip or other markings so as to contain an alpha numerical identification number which can be accessed in a rapid manner by a care given or emergency medical worker, and which provides a unique serial number to the wearer of the device.

7. The apparatus of claim 2 where in the outer protective shell contains grooves or slots for providing a positive mechanical alignment of the device to a mating unit to align the optical eyes for receiving and transmitting data, and to align the power contacts or pads for transmitting electrical power to the device and recharging of the battery, and updating digital data stored within the device, or erasing data from the device.

8. The apparatus of claim 2 wherein the outer protective shell can be of a electrically conductive material so as to act as an antenna for the transmission of radio waves from the transponder device so as to aid in locating the wearer of the device.

9. The apparatus of claim 2 wherein the outer protective shell is coated on its interior with a Radio Frequency coating shield so that the device will be able to transmit transponder signals while at the same time not interfering with the electronics and logic within the device.

10. The apparatus of claim 1 wherein the digital storage media is large enough and of the appropriate density to store large amounts of medical information such as x-rays, CAT scans, blood records, EKG record, dental records, allergic reaction information, living will instructions, photo ID or family contact information, and other medical information, emergency information, or personal identification information useful in an emergency.

11. The apparatus of claim 1 wherein the wireless sending and receiving of digital records and information to and from the device is done by a non-contact laser optical eye capable of writing, erasing and re-writing digital data to the bodily worn device.

12. The apparatus of claim 1 wherein a long life battery is mounted within the device for powering the electronics of the device and said battery can either be rechargeable or non-rechargeable.

13. The apparatus of claim 1 wherein the device is capable of receiving electrical power to the device by non-contact means, which may include mounting the secondary coils of a transformer within the device and providing electrical pads to mate in a non-contact manner with electrical pads connected to the primary coils of said transformer so as to lessen or eliminate the need for a battery within the device.

14. The apparatus of claim 13 wherein the secondary coils of the transformer are within the RFID chip capacitor and RF antenna mounted on the transformer receives the power signal and routes power to the RF storage chip for operation.

15. The apparatus of claim 1 wherein the transponder within the device is capable of emitting a high frequency signal which can be used to track and locate the wearer of the device in the event the wearer is lost, injured or deceased.

16. The apparatus of claim 1 wherein the outer protective shell can be opened to perform routine maintenance on the device, replace batteries, and perform service functions.

17. The apparatus of claim 1 wherein the outer protective shell can be filled with a shock absorbent polymer, rubber or other appropriate non-conductive material to mechanically stabilize and cushion the electronics and inner components of the device to further make the device shock resistant, explosion resistant and to ensure the device continues to operate during and after a disaster, catastrophic event or other high impact.

18. The apparatus of claim 1 wherein the exterior of the device contains either a watch, jewelry, watchband, and or other cosmetic features so as to mask or hide the true nature of the device for cosmetic reasons of the wearer or due to law enforcement or military secrecy.

19. The apparatus of claim 18 wherein the watchband, necklace or other cosmetic feature contains an RF antenna to aid the device in receiving and transmitting RF data signals.

20. The apparatus of claim 1 wherein the device contains a printer circuit board or miniature circuit for mounting electronic components within the device and electrically connecting said components so that all the components function as integrated electronic device.

21. The apparatus of claim 1 wherein the device contains an electronic logic computer chip which is capable of providing software logic for the device to organize the digital records into pages and usable information, monitor the battery charge life, and monitor the flow of digital data to and from the device.

22. The apparatus of claim 1 wherein the device contains an input-output jack, mounted to the inner printed circuit board, and protruding through the outer protective shell, which allows an emergency medical worker or other person to plug a mating jack into the device to transmit data to the device and receive data from the device in a rapid fashion.

23. The apparatus of claim 1 wherein the wireless means of sending and receiving stored medical records data is a radio frequency data carrier signal and data transfer occurs via a radio frequency field which is emitted by the reader/write unit and which creates a radio frequency data signal carrier path.

24. The apparatus of claim 23 wherein the RF carrier signal is a combination RF power carrier signal and RF data carrier signal for simultaneously sending electrical power to the passive RF chip and sending and receiving digital data.

25. The apparatus of claim 1 wherein the electronic transponder is capable of sending and receiving a radio frequency data carrier signal capable of transmitting digital medical records data and other digital data as described herein.

26. The apparatus of claim 1 wherein the digital storage media is a passive RFID—Radio Frequency Information Device type chip which is capable of storing digital information and transmitting it in a wireless fashion using a radio frequency carrier signal and said chip does not require any on-board battery to perform its data storage functions.

27. The apparatus of claim 26 wherein the RFID passive chip contains a charging capacitor for storing the transmitted electrical power to operate the device.

28. The apparatus of claim 27 wherein the charging capacitor contains a RF antenna for receiving power signals from the reader/writer RF field.

29. The apparatus of claim 26 wherein the RFID passive storage chip contains ferroelectric memory cells which operate within a specific voltage range.

30. The apparatus of claim 1 wherein the means of supplying power to the passive RF—Radio Frequency chip digital storage media is a combination power RF carrier signal and data carrier RF signal.

31. The apparatus of claim 1 wherein the protective outer shell of the device contains and RF antenna which allows the device to receive both RF power carrier signals and RF data carrier signals and to transmit RF data back to the read/write device.

32. A method for storing and retrieving digital records and data from a device carried or worn on a body of a user providing a digital storage apparatus comprising an outer shell or frame for mounting and protecting electronics stored within the shell, and providing a high capacity digital storage media which has write, erase and re-write data capabilities, and providing one half of a transformer coil with a contact for receiving and distributes electrical power to the device through a printed circuit which is mounted on a printed circuit board, and transferring and receiving data from interface wand to the data storage device via a laser optical eye arrangement, and erasing and re-writing and/or updating new digital data to the device digital storage device via the laser optical device, and transmitting and receiving digital data to and from the bodily worn device via a wireless Radio Frequency carrier signal, and providing a transponder unit which emits a high frequency carrier signal to allow the user of the device to be tracked and located.

33. The method of claim 32 further including a laser optical eye wand for transmitting and receiving digital data to and from the bodily worn device and said laser wand is capable of writing, erasing and re-writing digital data to the device.

34. The method of claim 33 further including mounting the device to or within a watch and watch band, or mounting the device within jewelry or mounting the device within a necklace pendant to conceal the nature of the device for the wearer.

35. The method of claim 34 wherein the watchband, necklace or other cosmetic feature contains an RF antenna to allow the device to receive and transmit RF data and power signals.

36. The method of claim 32 further including a printer circuit board with an electronic circuit grid for transmitting digital information, logic signals and electrical power to and from the electronic components mounted to the device.

37. The method of claim 32 further including a long life battery capable of being recharged so as to supply electric power to the logic device, and optical laser eye, and digital storage device and other device components on an as needed basis so the device may conserve electrical power.

38. The method of claim 32 further including a transponder device which emits radio frequencies of sufficient power which are capable of being received by long distance devices for the purpose of tracking and locating the wearer of the bodily worn device.

39. The method of claim 32 further including a logic chip which regulates the flow of digital data to and from optical jack input-output devices, data transmission contacts, and storage device to ensure that the digital data is not corrupted, and is routed to the proper component.

40. The method of claim 39 further including introducing a molding component into the outer protective shell and/or molding the electronic components in place to ensure mechanical stability so as to make the device shock proof and explosion proof and fire proof and water proof.

41. The method of claim 32 further including a digital storage device which receives, stores and transmits digital data based on logic signals from the device computer logic chip.

42. The method of claim 32 further including a data input-data output jack which allows new or updated digital data to be transmitted to the device via an external wire and jack assembly, and allows data to be transmitted from the device via an external wire and jack assembly.

43. The method of claim 32 further including a bar code strip mounted to the exterior of the device which would contain and alpha numerical identification serial number unique to the wearer of the device to identify the wearer of the device.

44. The method of claim 32 further including alpha numerical markings on the exterior of the device which would form a unique serial number to identify the wearer of the device and designate the medical condition or the wearer of the device and designate the military or law enforcement rank of the wearer of the device.

45. The method of claim 32 further including a means of color coding the exterior of the device to designate the medical severity of the wearer of the device and to designate the military or law enforcement rank of the wearer of the device.

46. The method of claim 32 further including electrical contacts mounted to the exterior of the device that would connect to the secondary coils of a transformer mounted within the device and said electrical contacts are capable receiving electrical power in a non-contact manner when placed in proximity to the mating primary coils of said transformer, which completes the transformer circuit.

47. The method of claim 46 further including mechanical alignment slots or tabs on the device which would mate with mechanical alignment slots or tabs on the interface wand to ensure proper mechanical alignment of the optical laser eye and electrical contacts.

48. The method of claim 46 wherein the secondary coils of said transformer are mounted within the RFID chip capacitor and an RF antenna mounted on said secondary transformer receives the RF power signal.

49. The method of claim 32 further comprising a system for transferring said digital data from the bodily worn device via a non-contact interface wand and displaying said digital data on a portable computer device screen in order of medical priority for rapid and effective medical treatment of said user and transmitting said data via wireless means to a base unit located in a hospital or clinical or other emergency medical treatment centers.

50. The method of claim 32 further including physically separating the electrical power and data files into two electrical circuit grids to avoid electrical interference and corruption of the data files.

51. The method of claim 32 whereby the computer logic chip regulates the flow of electrical power and digital data to avoid data corruption and interference.

52. The method of claim 32 whereby said computer logic chip is capable of recognizing an unique user serial number embedded in the device for user security and if said serial number is not matched during data write, erase, re-write, and access sequences, then said data commands are not performed.

53. The method of claim 32 wherein wireless data transfer occurs between the bodily worn device and the interface wand via an RF field which is emitted by the reader/write unit creating a bi-directional RF data signal carrier path.

54. The method of claim 53 wherein the RF carrier signal is capable of simultaneously transmitting an asynchronous RF power signal and RF data signal via the RF carrier field.

55. The method of claim 53 wherein the RFID passive chip contains a charging capacitor for storing electrical power received from the RF power carrier signal.

56. The method of claim 55 wherein the charging capacitor contains a RF antenna for receiving RF power signals from said RF field.

57. The method of claim 32 wherein the electronic transponder is capable of sending and receiving user medical records via the RF-radio frequency data carrier signal.

58. The method of claim 32 wherein the digital storage media is a passive RFID—Radio Frequency Information Device chip which is capable of storing digital information and transmitting it in a wireless fashion using said RF carrier signal and said chip does not require an on-board battery or power source to perform its data storage functions.

59. The method of claim 58 wherein the RFID passive storage chip contains ferroelectric memory cells which operate within a specific voltage range.

60. The method of claim 32 wherein the means of supplying power and data to the passive RF chip digital storage media is an asynchronous RF power carrier signal and RF data carrier signal which are alternately transmitted in discrete pulsed signals.

61. The method of claim 32 wherein the protective outer shell of the device contains and RF antenna which allows the device to receive both RF power carrier signals and RF data carrier signals in a pulsed and asynchronous fashion and to transmit RF data back to the read/write wand device.

* * * * *